United States Patent [19]

Reiffen et al.

[11] Patent Number: 5,026,702
[45] Date of Patent: Jun. 25, 1991

[54] MORPHOLINES AND MORPHOLINE-N-OXIDES AND PHARMACEUTICAL COMPOSITIONS CONTAINING THESE COMPOUNDS

[75] Inventors: Manfred Reiffen; Michael Mark, both of Biberach; Robert Sauter, Laupheim; Wolfgang Grell, Biberach, all of Fed. Rep. of Germany

[73] Assignee: Dr. Karl Thomae, GmbH, Biberach an der Riss, Fed. Rep. of Germany

[21] Appl. No.: 327,665

[22] Filed: Mar. 23, 1989

[30] Foreign Application Priority Data

Mar. 23, 1988 [DE] Fed. Rep. of Germany ......... 3809775

[51] Int. Cl.$^5$ .................. A61K 31/535; C07D 413/04
[52] U.S. Cl. ................................. 514/235.5; 514/212; 514/230.8; 514/235.8; 514/236.5; 540/601; 540/598; 544/114; 544/120; 544/121; 544/122; 544/124; 544/129; 544/141
[58] Field of Search ............... 544/114, 120, 122, 124, 544/129, 141, 121; 514/230.8, 235.5, 235.8, 236.5, 212; 540/601, 598

[56] References Cited

FOREIGN PATENT DOCUMENTS 0140359 5/1985 European Pat. Off. .
2121031 4/1971 Fed. Rep. of Germany .
868987 5/1961 United Kingdom ................ 544/129

Primary Examiner—Mary C. Lee
Assistant Examiner—Jacqueline Haley
Attorney, Agent, or Firm—D. E. Frankhouser; M-E. M. Timbers; A. R. Stempel

[57] ABSTRACT

The invention relates to new morpholines and morpholine-N-oxides of formula

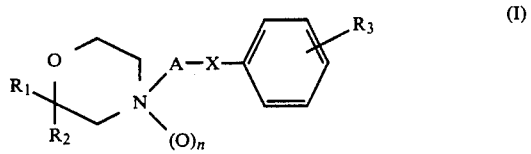

wherein the substituents are defined hereunder, which compounds have valuable pharmacological properties, namely an effect on the metabolism, preferably the effect of lowering blood sugar and reducing body fat, and the effect of lowering the atherogenic β-lipoproteins VLDL and LDL, and a performance enhancing effect in animals.

22 Claims, No Drawings

MORPHOLINES AND MORPHOLINE-N-OXIDES AND PHARMACEUTICAL COMPOSITIONS CONTAINING THESE COMPOUNDS

The present invention relates to new morpholines and morpholine-N-oxides of formula

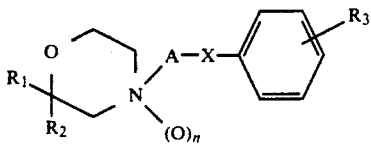

the optical isomers and diastereomers thereof, since the new compounds contain one or more optically active carbon atoms, and the acid addition salts thereof, particularly for pharmaceutical use the physiologically acceptable acid addition salts thereof with inorganic or organic acids, which have valuable pharmacological properties, namely an effect on metabolism, preferably the effect of lowering blood sugar and reducing body fat, and the effect of lowering the atherogenic lipoproteins VLDL and LDL. In addition, some of the compounds mentioned above also have an anabolic effect.

In the above formula

A represents an n-alkylene group having 2 or 3 carbon atoms optionally mono- or disubstituted by methyl or ethyl groups, X represents a bond or an oxygen atom, $R_1$ represents a heteroaromatic 6-membered ring containing 1 or 2 nitrogen atoms and optionally substituted by a halogen atom or by hydrogen or a trifluoromethyl or alkyl group, $R_2$ represents a hydrogen atom or a hydroxy group, $R_3$ represents a hydroxy, alkoxy, carboxy, alkoxycarbonyl, aminocarbonyl, alkylaminocarbonyl or dialkylaminocarbonyl group, an alkoxy group with 1 to 6 carbon atoms substituted in the end position by a carboxy, alkoxycarbonyl, aminocarbonyl, alkylaminocarbonyl or dialkylaminocarbonyl group, an alkoxy group having 2 to 7 carbon atoms substituted in the end position by a hydroxy, alkoxy or phenylalkoxy group, or an ethenylene group optionally substituted by an alkyl group and substituted in the end position by a carboxy, alkoxycarbonyl, aminocarbonyl, alkylaminocarbonyl, dialkylaminocarbonyl, pyrrolidino, piperidino or hexamethyleneimino group, and n represents the number 0 or 1,
whilst all the alkyl or alkoxy groups mentioned hereinbefore may contain from 1 to 3 carbon atoms.

As examples of the definitions of the groups mentioned hereinbefore:

A may represent an ethylene, 1-methyl-ethylene, 2-methyl-ethylene, 1-ethyl-ethylene, 2-ethylene-ethylene, 1,2-dimethyl-ethylene, 1,1-dimethyl-ethylene, 1,1-diethyl-ethylene, 1-ethyl-1-methyl-ethylene, 2,2-dimethyl-ethylene, 2,2-diethyl-ethylene, 2-ethyl-2-methyl-ethylene, n-propylene, 1-methyl-n-propylene, 2-methyl-n-propylene, 3-methyl-n-propylene, 1-ethyl-n-propylene, 2-ethyl-n-propylene, 3-ethyl-n-propylene, 1,1-dimethyl-n-propylene, 1,1-diethyl-n-propylene, 2,3-dimethyl-n-propylene, 3,3-dimethyl-n-propylene or 3-ethyl-3-methyl-n-propylene group, $R_1$ may represent a pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 2-chloro-pyridin-6-yl, 2-chloro-pyridin-4-yl, 2-bromo-pyridin-4-yl, 2-bromo-pyridin-6-yl, 3-chloro-pyridin-5-yl, 3-bromo-pyridin-5-yl, 2-trifluoromethyl-pyridin-4-yl, 2-trifluoromethyl-pyridin-6-yl, 2-methyl-pyridin-4-yl, 2-ethyl-pyridin-4-yl, 2-propyl-pyridin-4-yl, 2-isopropyl-pyridin-4-yl, 3-methyl-pyridin-2-yl, 4-methyl-pyridin-2-yl, 2-methyl-pyridin-3-yl, 4-methyl-pyridin-3-yl or 3-methyl-pyridin-5-yl group, $R_2$ may represent a hydrogen atom or a hydroxy group, X may represent an oxygen atom or a bond and $R_3$ may represent a hydroxy, methoxy, ethoxy, n-propoxy, isopropoxy, carboxy, methoxycarbonyl, ethoxycarbonyl, n-propoxycarbonyl, aminocarbonyl, methylaminocarbonyl, ethylaminocarbonyl, isopropylamino-carbonyl, dimethylaminocarbonyl, diethylaminocarbonyl, di-n-propylaminocarbonyl, N-ethyl-methylaminocarbonyl, N-ethyl-isopropylaminocarbonyl, 2-hydroxy-ethoxy, 3-hydroxy-n-propoxy, 4-hydroxy-n-butoxy, 5-hydroxy-n-pentoxy, 6-hydroxy-n-hexoxy, 7-hydroxy-n-heptoxy, 2-methoxy-ethoxy, 2-ethoxy-ethoxy, 2-n-propoxy-ethoxy, 3-ethoxy-n-propoxy, 4-methoxy-n-butoxy, 6-ethoxy-n-hexoxy, 2-phenethoxy-ethoxy, carboxymethoxy, 2-carboxy-ethoxy, 3-carboxy-n-propoxy, 4-carboxy-n-butoxy, methoxycarbonylmethoxy, 2-methoxycarbonyl-ethoxy, 6-methoxycarbonyl-hexoxy, ethoxycarbonylmethoxy, 2-ethoxycarbonyl-ethoxy, 3-ethoxycarbonyl-n-propoxy, n-propoxycarbonylmethoxy, 2-isopropoxycarbonylethoxy, 4-n-propoxycarbonyl-n-butoxy, aminocarbonylmethoxy, 2-aminocarbonylethoxy, 4-aminocarbonyl-n-butoxy, methylaminocarbonylmethoxy, 2-methylamino-carbonyl-ethoxy, dimethylaminocarbonylmethoxy, 2-dimethylaminocarbonylethoxy, 4-dimethylaminocarbonyl-n-butoxy, diethylaminocarbonyl-methoxy, 2-diethyl-aminocarbonylethoxy, 2-di-n-propyl-aminocarbonyl-ethoxy, 2-carboxy-ethenyl, 2-carboxy-1-methyl-ethenyl, 2-carboxy-2-methyl-ethenyl, 2-carboxy-1-ethyl-ethenyl, 2-carboxy-1-n-propyl-ethenyl, 2-methoxycarbonyl-ethenyl, 2-methoxycarbonyl-1-methyl-ethenyl, 2-ethoxycarbonyl-ethenyl, 2-ethoxycarbonyl-1-methyl-ethenyl, 2-isopropoxycarbonyl-ethenyl, 2-pyrrolidino-ethoxy, 2-piperidino-ethoxy or 2-hexamethyleneimino-ethoxy group.

The following compounds covered by general formula I mentioned hereinbefore may also be cited in addition to the compounds mentioned in the Examples:

N-[2-(4-carboxymethoxyphenyl)-1-methylethyl]-2-(6-trifluoromethyl-pyridin-2-yl)-morpholine, N-[2-(4-carbomethoxymethoxyphenyl)-1-methylethyl]-2-(6-trifluoromethyl-pyridin-2-yl)-morpholine, N-[2-(4-(2-hydroxy-ethoxy)-phenyl)-1-methylethyl]-2-(6-trifluoromethyl-pyridin-2-yl)-morpholine, N-[2-(4-carbomethoxymethoxyphenyl)--1-methylethyl]-2-hydroxy-2-(6-chloro-pyridin-2-yl)-morpholine, N-[2-(4-carboxymethoxyphenyl)-1-methylethyl]-2-hydroxy-2-(6-chloro-pyridin-2-yl)-morpholine, N-[2-(4-(2-hydroxy-ethoxy)-phenyl)-1-methylethyl]-2-hydroxy-2-(6-chloro-pyridin-2-yl)-morpholine, N-[2-(4-(2-carbomethoxy-1-methylethenyl)-phenyl)-1-methylethyl]-2-(6-methyl-pyridin-2-yl)-morpholine, N-[2-(4-carbomethoxymethoxy-phenoxy)-ethyl]-2-(6-methyl-pyridin-2-yl)-morpholine, N-[2-(4-(2-(1-piperidino)-ethoxy)-phenyl)-1-methylethyl]-2-(6-chloro-pyridin-2-yl)-morpholine, N-[2-(4-aminocarbonylmethoxy-phenyl)-1-methylethyl]-2-(6-chloro-pyridin-2-yl)-morpholine, N-[2-(4-methylaminocarbonylmethoxy-phenyl)-1-methylethyl]-2-(6-chloro-pyridin-2-yl)-morpholine, N-[2-(4-(2-ethoxy-ethoxy)-phenyl)-1-methylethyl]-2-(6-chloro-pyridin-2-yl)-morpholine, N-[2-(4-carboxymethoxy-phenyl)-1-methylethyl]-2-(6-chloro-pyridin-2-yl)-morpholine, N-[2-(4-carboxy-phenyl)-1-methylethyl]-2-(6-chloro-pyridin-2-yl)-morpholine, N-[2-(4-(2-(2-phenylethoxy)-ethoxy)-phenyl)-1-methylethyl]-2-(6-chloro-pyridin-2-yl)-morpholine and N-[2-(4-(6-hydroxy-n-hexoxy)-phenyl)-1-methylethyl]-2-(6-chloro-pyridin-2-yl)-morpholine, the optical isomers, diastereoisomers and acid addition salts thereof.

However, the preferred compounds are the compounds of formula I wherein n is defined as hereinbefore, A represents an ethylene or n-propylene group optionally substituted by a methyl group, X represents a bond, $R_1$ represents a pyridinyl group optionally substituted by a chlorine or bromine atom, or a pyrazinyl, pyrimidinyl or pyridazinyl group, $R_2$ represents a hydrogen atom or a hydroxy group and $R_3$ represents a carboxy, methoxycarbonyl, ethoxycarbonyl, aminocarbonyl, carboxymethoxy, methoxycarbonylmethoxy, ethoxycarbonylmethoxy, aminocarbonylmethoxy, methylaminocarbonylmethoxy, 2-hydroxy-ethoxy, 2-ethoxy-ethoxy, 2-phenethoxy-ethoxy, 6-hydroxy-n-hexoxy or 2-carbomethoxy-1-methyl-ethenyl group, the optical isomers, diastereoisomers and acid addition salts thereof.

However, particularly preferred compounds are the compounds of formula

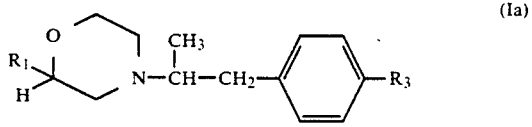

(Ia)

wherein $R_1$ represents a pyridin-2-yl group substituted in the 6-position by a chlorine or bromine atom or by a methyl or trifluoromethyl group and $R_3$ represents a carboxymethoxy, carbomethoxymethoxy, ethoxycarbonylmethoxy, aminocarbonylmethoxy, methylaminocarbonylmethoxy, 2-hydroxy-ethoxy, 2-ethoxy-ethoxy or 2-carbomethoxy-1-methyl-ethenyl group, the optical isomers, diastereoisomers and acid addition salts thereof.

According to the invention, the new compounds are obtained by the following processes:

(a) in order to prepare compounds of formula I wherein n represents the number 0:

reaction of a ketone of formula

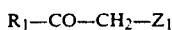

(II)

wherein $R_1$ is as hereinbefore defined and $Z_1$ represents a nucleophilic leaving group, with an ethanolamine of formula

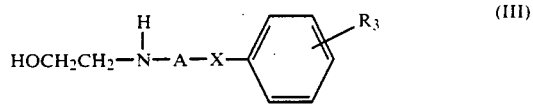

(III)

wherein $R_3$, A and X are as hereinbefore defined, and in order to prepare a compound of formula I wherein $R_2$ represents a hydrogen atom, reduction of a compound of formula

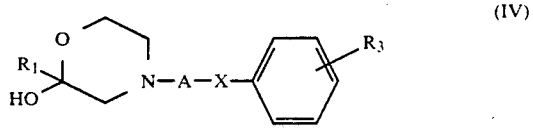

(IV)

thus obtained, wherein $R_1$, $R_3$, A and X are defined as hereinbefore, optionally with subsequent hydrolysis of an ester thus obtained.

Examples of nucleophilic leaving groups include halogen atoms or sulphonyloxy group, e.g. a chlorine, bromine or iodine atom or the methanesulphonyloxy, p-toluenesulphonyloxy or ethoxysulphonyloxy group.

The reaction is conveniently carried out in a suitable solvent such as acetone, methylene chloride, tetrahydrofuran or dioxan and preferably in the presence of an acid-binding agent such as potassium hydrogen carbonate, potassium carbonate, sodium hydrogen carbonate, sodium carbonate, triethylamine or pyridine, whilst the organic acid binding agents may simultaneously also be used as solvents, at temperatures of between 0° and 100° C., preferably at temperatures between 5° and 50° C.

The subsequent reduction of a compound of formula IV necessary in order to prepare a compound of formula I wherein $R_2$ represents a hydrogen atom and n represents the number 0 is preferably carried out in a solvent such as methylene chloride, chloroform, trifluoroacetic acid or trifluoromethanesulphonic acid with a suitable hydride such as a complex metal hydride, e.g. sodium borohydride, with catalytically activated hydrogen, e.g. with hydrogen in the presence of platinum, or a trialkylsilane, e.g. with triethylsilane, optionally in the presence of an acid such as boron trifluoride, e.g. in the presence of boron trifluoride etherate, at temperatures of between 0° and 60° C., but preferably in trifluoroacetic acid as solvent and at ambient temperature.

The optional subsequent ester cleavage is preferably carried out by hydrolysis in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures between 0° and 100° C., preferably at the boiling temperature of the reaction mixture.

(b) In order to prepare compounds of formula I wherein n represents the number 0 and $R_2$ represents a hydrogen atom:

reductive amination of a carbonyl compound of formula

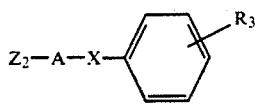 (V)

wherein
$R_3$, A and X are defined as hereinbefore and
$Z_2$ together with a hydrogen atom of the adjacent carbon atom of the group A represents an oxygen atom, with an amine of formula

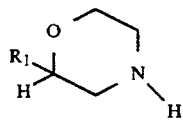 (VI)

wherein $R_1$ is as hereinbefore defined.

The reductive amination is carried out in a suitable solvent such as methanol, ethanol, tetrahydrofuran, dioxan or acetonitrile in the presence of a suitable reducing agent such as a suitable complex metal hydride, but preferably in the presence of sodium cyanoborohydride at a pH of from 5 to 7, at temperatures of between 0° and 50° C., but preferably at ambient temperature.

(c) In order to prepare compounds of general formula I wherein n represents the number 0 and $R_2$ represents a hydrogen atom:
reduction of a compound of general formula

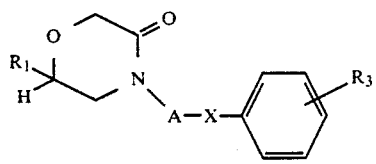 (VII)

wherein A, X, $R_1$ and $R_3$ are as hereinbefore defined.

The reduction is carried out in a suitable solvent such as diethylether or tetrahydrofuran with a reducing agent such as a metal hydride, e.g. with lithium aluminium hydride or sodium borohydride in the presence of glacial acetic acid or trifluoroacetic acid, but preferably with phosphorus oxychloride/sodium borohydride, diborane or diborane/dimethylsulphide at temperatures of between 0° and 50° C., but preferably at temperatures of between 10° and 25° C. During the reduction, any carbonyl function present in the group $R_3$ can simultaneously be reduced to a methylene group.

(d) In order to prepare compounds of formula I wherein n represents the number 0, $R_2$ represents a hydrogen atom and $R_3$ represents an alkoxy group having 1 to 3 carbon atoms, an alkoxy group having 1 to 6 carbon atoms substituted in the end position by a carboxy, alkoxycarbonyl, aminocarbonyl, alkylamino-carbonyl or dialkylaminocarbonyl group, or an alkoxy group with 2 to 7 carbon atoms substituted in the end position by a hydroxy, alkoxy, amino, alkylamino, dialkylamino, pyrrolidino, piperidino or hexamethyleneimino group:
reaction of a compound of formula

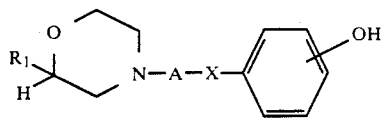 (VIII)

wherein $R_1$, A and X are defined as hereinbefore, with a compound of formula $$Z_3\text{-}R_4 \quad (IX)$$

wherein
$R_4$ represents an alkyl group having 1 to 3 carbon atoms, an alkyl group having 1 to 6 carbon atoms substituted in the end position by a carboxy, alkoxycarbonyl, aminocarbonyl, alkylaminocarbonyl or dialkylaminocarbonyl group, or an alkyl group having 2 to 7 carbon atoms substituted in the end position by a hydroxy, alkoxy, amino, alkylamino, dialkylamino, pyrrolidino, piperidino or hexamethyleneimino group, and $Z_3$ represents a nucleophilic leaving group such as a halogen atom or a sulphonyloxy group, e.g. a chlorine, bromine or iodine atom, the methanesulphonyloxy, p-toluenesulphonyloxy or ethoxysulphonyloxy group, or $Z_3$ together with a beta-hydrogen atom of the group $R_4$ represents an oxygen atom.

The reaction is conveniently carried out in a solvent such as diethylether, tetrahydrofuran, dioxan, methanol, ethanol or dimethylformamide and preferably in the presence of an acid binding agent such as sodium hydroxide or potassium tert.butoxide, but preferably in the presence of potassium carbonate or sodium hydride, or pyridine, whilst an organic base such as pyridine may also be used as solvent, or in order to prepare 2-hydroxy-ethoxy compounds of general formula I, with ethylene oxide at temperatures of between 0 and 100° C., but preferably at temperatures of between 20° and 80° C.

(e) In order to prepare compounds of formula I wherein n represents the number 0 and $R_3$ represents or contains an alkoxycarbonyl, aminocarbonyl, alkylaminocarbonyl or dialkylaminocarbonyl group:
reaction of a compound of formula

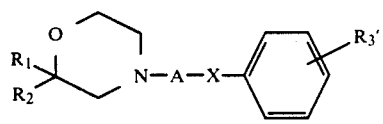 (X)

wherein
$R_1$, $R_2$, A and X are as hereinbefore defined and
$R_3'$ represents a carboxy group or an alkoxy group having 1 to 6 carbon atoms, substituted in the end position by a carboxy group, or the reactive derivatives thereof such as, for example, the esters thereof, with a compound of formula $$H\text{—}R_5 \quad (XI)$$

wherein $R_5$ represents an alkoxy, amino, alkylamino or dialkylamino group, whilst the alkyl or alkoxy part may contain from 1 to 3 carbon atoms.

The esterification or amidation is conveniently carried out in a solvent such as methylene chloride, chloroform, carbon tetrachloride, ether, tetrahydrofuran, dioxan, benzene, toluene, acetonitrile or dimethylformamide, but particularly advantageously in an excess of the compound of general formula X used, e.g. in methanol, ethanol, n-propanol, isopropanol, ammonia, methylamine, ethylamine, dimethylamine or diethylamine, optionally in the presence of an acid-activating agent or a dehydrating agent, e.g. in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxy-succinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which may simultaneously serve as solvent, at temperatures of between $-25°$ C. and 250° C., but preferably at temperatures between $-10°$ C. and the boiling temperature of the solvent used.

(f) In order to prepare the compounds of formula I wherein n represents the number 1:
reaction of a compound of formula

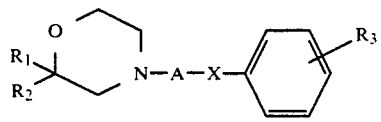

wherein $R_1$ to $R_3$, A and X are defined as hereinbefore, with a peroxy compound with optional subsequent hydrolysis.

The reaction is conveniently carried out in a solvent or mixture of solvents such as methylene chloride, chloroform, tetrahydrofuran, acetonitrile, water, methanol, ethanol, water/ethanol, glacial acetic acid or trifluoroacetic acid with a peroxy compound such as hydrogen peroxide, perbenzoic acid or m-chloroperbenzoic acid at temperatures of between 0° C. and the boiling temperature of the solvent used, preferably at temperatures of between 60° and 80° C. It is particularly advantageous to carry out the reaction using hydrogen peroxide in glacial acetic acid at temperatures between 60° and 80° C.

The optional subsequent hydrolysis is conveniently carried out in an aqueous solvent, e.g. in water, isopropanol/water, tetrahydrofuran/water or dioxan/water, preferably in the presence of an acid such as hydrochloric or sulphuric acid at temperatures of between 0° and 100° C., preferably at the boiling temperature of the reactior mixture.

In reactions (a) to (g) reactive groups may be protected during the reaction by conventional protecting groups which are split off again by conventional methods after the reaction.

Suitable protecting groups for a carboxy group include, for example, the benzyl, tert.butyl, tetrahydropyranyl, trimethylsilyl, benzyloxymethyl, 2-chloroethyl or methoxymethyl groups or a phenacyl group such as a benzoylmethyl group; suitable protecting groups for an amino or alkylamino group include the acetyl, benzoyl, tert.butoxycarbonyl, benzyloxycarbonyl, ethoxycarbonyl or benzyl groups; and suitable protecting groups for a hydroxy group include, for example, the trityl, fluorenylmethyloxycarbonyl, benzyloxycarbonyl or benzyl groups.

The optional subsequent splitting off of a protecting group is preferably carried out by hydrolysis in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl or benzyloxycarbonyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

If according to the invention a compound of formula I is obtained wherein $R_3$ represents or contains an alkoxycarbonyl, aminocarbonyl, alkylaminocarbonyl or dialkylaminocarbonyl group, this may be converted by hydrolysis into a corresponding compound of formula I wherein $R_3$ represents or contains a carboxy group, or if a compound of formula I is obtained wherein $R_3$ represents an alkoxy group substituted by a carboxy, alkoxycarbonyl, aminocarbonyl, alkylaminocarbonyl or dialkylaminocarbonyl group, this may be converted by reduction using a suitable metal hydride into a compound of general formula I wherein the above-mentioned substituted alkoxy group contains a methylene group instead of the carbonyl group, or if a compound of formula I is obtained wherein $R_3$ represents one of the alkoxy groups mentioned hereinbefore, this may be converted by ether cleavage into a corresponding compound of formula I wherein $R_3$ represents a hydroxy group or an alkoxy group substituted by a hydroxy group.

The subsequent hydrolysis is carried out either in the presence of an acid such as hydrochloric, sulphuric, phosphoric or trichloroacetic acid or in the presence of a base such as sodium hydroxide or potassium hydroxide in a suitable solvent such as water, methanol, ethanol, ethanol/water, water/isopropanol or water/dioxan at temperatures of between $-10°$ C. and 120° C., e.g. at temperatures of between ambient temperature and the boiling temperature of the reaction mixture.

The subsequent reduction is carried out in a suitable solvent such as diethylether or tetrahydrofuran with a suitable metal hydride, e.g. with lithium aluminium hydride, diborane or diborane/dimethylsulphide, but preferably with sodium borohydride in the presence of glacial acetic acid or trifluoroacetic acid, at temperatures between 0° and 50° C., but preferably at temperatures between 10° and 25° C.

The subsequent ether cleavage is carried out in the presence of an acid such as hydrochloric, hydrobromic, sulphuric acid or boron tribromide in a suitable solvent such as methanol, ethanol, water/isopropanol, methylene chloride, chloroform or carbon tetrachloride at temperatures of between $-30°$ C. and the boiling temperature of the reaction mixture.

As already mentioned hereinbefore, the new compounds may occur in the form of their enantiomers, mixtures of enantiomers or racemates or, if they contain at least two asymmetric carbons, they may also occur in the form of their pairs of diastereoisomers or mixtures of pairs of diastereoisomers.

Thus, the compounds of formula I obtained which contain only one optically active centre may be resolved by known methods (see Allinger N. L. and Eliel W. L. in "Topics in Stereochemistry", Vol. 6, Wiley Interscience, 1971) into their optical antipodes, e.g. by recrystallisation from an optically active solvent or by reaction with an optically active substance which forms salts with the racemic compound, more particularly an acid, and separation of the mixture of salts thus obtained, e.g. on the basis of their different solubilities, into the diastereoisomeric salts from which the free antipodes can be liberated by reaction with suitable substances.

Examples of particularly common optically active acids include the D- and L-forms of tartaric acid, di-o-toluene tartaric acid, malic acid, mandelic acid, camphorsulphonic acid, glutamic acid, aspartic acid or quinic acid.

Furthermore, the compounds of formula I obtained having at least 2 asymmetric carbon atoms may be separated, on the basis of their physical/chemical differences into their diastereoisomers using methods known per se, e.g. chromatography and/or fractional crystallisation. A pair of enantiomers thus obtained may subsequently be resolved into the optical antipodes thereof as described above. If for example a compound of general formula I contains two optically active carbon atoms, the corresponding (R R', S S') and (R S', S R') forms are obtained or, if it has 3 optically active centres, the corresponding (R R' R", S S' S"), (R S' R", S R' S"), (S R' R", R S' S") and (R R' S", S S' R") forms are obtained.

The compounds used as starting materials which can obviously also be used in their optically pure forms are obtained by methods known from the literature or are themselves known from the literature. Some of these occur only in the reaction mixture and therefore cannot be isolated.

For example, a compound of formula VIII or X used as starting material is obtained by alkylation of a corresponding morpholine and optionally subsequently splitting off any protecting group used.

The compounds of formula VII used as starting materials are obtained by reaction of the compounds of formula

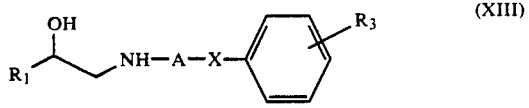

(XIII)

(wherein $R_1$, A, X and $R_3$ are defined as hereinbefore), described in EP-A-No. 0239815, with a haloacetylchloride or a corresponding haloacetic ester.

The reaction is conveniently carried out in a solvent such as methylene chloride, tetrahydrofuran, dioxan, benzene or toluene or in an excess of the acylating agent used, optionally in the presence of an acid-binding agent such as potassium carbonate, an alkali metal hydride such as sodium hydride or in the presence of a tertiary organic base such as triethylamine or pyridine, whilst the latter two may simultaneously also be used as solvent, at temperatures between 0° and 100° C., but preferably at temperatures between ambient temperature and the boiling temperature of the reaction mixture.

Furthermore, the compounds of formula I obtained may be converted into the acid addition salts thereof, particularly for pharmaceutical use into the physiologically acceptable salts thereof with inorganic or organic acids. Examples of suitable acids include hydrochloric, hydrobromic, sulphuric, phosphoric, fumaric, succinic, lactic, citric, tartaric or maleic acids.

As already mentioned hereinbefore, the new compounds of formula I, the enantiomers, mixtures of enantiomers or racemates thereof or, if they have at least two asymmetric carbon atoms, the diastereoisomers or mixtures of diasteroisomers, and acid addition salts thereof, more particularly for pharmaceutical use the physiologically acceptable acid addition salts thereof, have valuable pharmacological properties, not only an inhibiting effect on platelet aggregation but more particularly an effect on the metabolism, preferably the effect of lowering blood sugar and reducing body fat, and the effect of lowering the atherogenic beta-lipoproteins VLDL and LDL. In addition, some of the compounds mentioned hereinbefore also have an anabolic activity. Of the compounds of Examples 3 to 6, the diastereoisomer in which the proton resonance signal of the methyl group which is adjacent to the morpholine nitrogen atom is in the lower area in the $CDCl_3/CD_3OD$-NMR spectrum has proved particularly preferable.

The biological properties of the new compounds have been investigated as follows:

1. Antidiabetic activity:

The antidiabetic activity of the compounds according to the invention can be measured as a blod sugar-lowering activity in experimental animal. The substances to be tested were suspended in 1.5% methyl cellulose and administered by oesophageal tube to female mice bred by the applicants. 30 minutes later, 1 g of glucose per kg of body weight dissolved in water was administered subcutaneously. Another 30 minutes later blood was taken from the retroorbital venous plexus. From the serum, glucose was determined by the hexokinase method using an analytical photometer.

The Table which follows summarises the reductions in blood sugar observed in this test as a percentage of a parallel control group. Statistical evaluation was carried out by the Student's t-test taking $p=0.05$ as the limit of significance

| Compound (Example No.) | % Change from the value of the control group Dosage [mg/kg] 0.3 |
|---|---|
| 3 | −50 |
| 4 | −58 |
| 6 | −65 |

2. Antiadipose activity:

The antiadipose activity of the compounds according to the invention was demonstrated by two tests:

(a) In the first test the increase in lipolysis was measured by the rise in the glycerol in the serum. The test procedure is identical to that described hereinbefore for testing for a reduction in blood sugar. Glycerol was determined in a combined enzymatic-colorimetric test using an analytical photometer. The results are shown in the following Table as a percentage of a parallel control group.

| Compound (Example No.) | % Change from the value of the control group Dosage [mg/kg] 0.3 |
|---|---|
| 3 | +262 |
| 4 | +221 |
| 6 | +314 |

(b) In the second test for determining the antiadipose activity of the compounds according to the invention, the reduction in fatty tissue was measured by taking as an example the fatty tissue around the ovary. For this purpose the compounds were administered to mice once a day by oesophageal tube in a 1.5% methyl cellulose suspension. On the fifth day the fatty tissue from the ovary was dissected out and weighed. The following Table shows the results as a percentage of a parallel control group.

| Compound (Example No.) | % Change from the value of the control group Dosage 1 [mg/kg] |
|---|---|
| 5 | −41 |

3. Cardiac side effects:

The occurrence of undesirable side effects on the heart was ruled out for the compounds according to the invention for the metabolically effective dosage range required for therapy. To demonstrate this, heart rate was measured in mice during the testing for the blood sugar reducing activity (see above). One hour after oral administration of the compounds the heart rate was determined by ECG-triggered tachograph. The Table which follows shows the change in heart rate as a percentage of the control group.

| Compound (Example No.) | % Change from the value of the control group | Dosage mg/kg |
|---|---|---|
| 3 | (+6) | 3.0 |
| 4 | (0) | 3.0 |
| 6 | (+4) | 3.0 |

( ) = not significant (p greater than 0.05)

Moreover, at the doses used, no toxic side effects were observed in the investigations of the substances according to the invention described above. These substances are therefore well tolerated.

In view of their pharmacological properties the new compounds of formula I and the physiologically acceptable acid addition salts thereof with inorganic or organic acids are therefore suitable for treating both diabetes mellitus and obesity, and particularly for treating obese diabetics. Furthermore, the new compounds may be used for the prevention and treatment of atherosclerotic changes in the blood vessels, which occur particularly in diabetics and the obese. The dosage required can be matched fully to the physiological metabolic requirements of the individual patient, since the substances are free from any effect on the heart or circulation over a wide dosage range. In adults the daily dosage is therefore between 1 and 3000 mg, preferably from 1 to 1000 mg, divided into 1 to 4 doses per day. For this purpose, the above-mentioned compounds, optionally combined with other active substances, may be incorporated in the usual galenic preparations such as powders, plain or coated tablets, capsules, suppositories or suspensions.

The compounds mentioned above may also be used to treat obese animals such as dogs and, as a result of their body fat-reducing (lipolytic) effect, they may be used to reduce undesirable fatty deposits in the fattening of animals, i.e. to improve the quality of the meat of fattened animals such as pigs, cattle, sheep and poultry. In animals, the compounds mentioned above may be administered by oral or non-oral route, e.g. as a feed additive or by injection or using implanted minipumps. The daily dose is between 0.01 and 100 mg/kg, but preferably between 0.1 and 10 mg/kg of body weight.

The active substances mentioned hereinbefore may also be used as performance enhancers in animals in order to promote and accelerate growth, milk and wool production, and to improve the utilisation of feed, the quality of the carcasses and in order to shift the ratio of meat to fat in favour of meat. The active substances are used in farm animals, animals for breeding and display as well as pets.

The farm animals and breeding animals include, for example, mammals such as cattle, pigs, horses, sheep, goats, rabbits, hares, deer, fur animals such as mink and chinchilla, poultry such as chickens, geese, ducks and turkeys, fish such as carp, trout, salmon, eels, tench and pike and reptiles such as snakes and crocodiles.

Display animals and pets include mammals such as dogs and cats, birds such as parrots, canaries, fish such as ornamental and aquarium fish, e.g. gold fish.

The active substances are used throughout all the growth and performance stages of the animal, irrespective of the sex of the animal. The active substances are preferably used during the intensive growth and performance phase. Depending on the type of animal the intensive growth and performance phase lasts for one month to 10 years.

The quantity of active substances administered to the animals in order to achieve the desired effect may vary substantially owing to the favourable properties of the active substances. It is preferably about 0.001 to 50 mg/kg, more particularly 0.01 to 5 mg/kg of bodyweight per day. The suitable quantity of active substance and the proper duration of administration will depend particularly on the type of animal, its age, sex, state of health and the manner of keeping and feeding the animals and can readily be determined by anyone skilled in the art.

The active substances are administered to the animals by the usual methods. The type of administration will depend particularly on the type of animal and its behaviour and state of health.

The active substances may be administered once. However, they may also be administered temporarily or continuously throughout the entire growth phase or during part of it. If they are administered continuously they may be given one or more times a day at regular or irregular intervals.

The substances are administered orally or parenterally in suitable formulations or in pure form. Oral formulations are powders, tablets, granules, drenches, boli and feedstuffs, premixes for feedstuffs, formulations for administering in drinking water.

The oral formulations contain the active substance in concentrations of from 0.01 ppm to 100%, preferably from 0.01 ppm to 10%.

Parenteral formulations are injections in the form of solutions, emulsions and suspensions, as well as implants.

The active substances may be present in the formulations on their own or in admixture with other active substances, mineral salts, trace elements, vitamins, proteins, colourings, fats or flavourings.

The concentration of active substances in the feed is normally about 0.01 to 500 ppm, preferably 0.1 to 50 ppm.

The active substances may be added to the feed as they are or in the form of premixes or feed concentrates.

Thus, in addition to the active substance and optionally a conventional vitamin/mineral mixture, the feedstuffs according to the invention contain for example, barley, wheat flour, broad beans, shredded rape extract and edible fat for fattening pigs; maize, soya flour, meatmeal, edible fat and soya oil for broilers; shredded sugar beet, maize gluten, malt germs, soya bean flour, wheat and molasses for cattle; and barley, soya bean flour, maize and molasses for lambs. One of the above-mentioned compounds of formula I is added as active substance to this feedstuff in a concentration of 0.01 to 500 ppm, but preferably from 0.1 to 50 ppm, preferably in the form of a premix of active substance. This premix contains, for example, 10 mg of active substance in 9.99 g of corn starch per 10 g.

The Examples which follow are intended to illustrate the invention:

EXAMPLE A

5-Bromo-3-acetyl-pyridine 44.2 g (0.276 mol) of diethylmalonate, 19.9 g (0.432 mol) of absolute ethanol and 7 g (0.288 mol) of magnesium chips are refluxed for 18 hours with stirring in 254 ml of ether and 1.27 ml of carbon tetrachloride. To this solution, 55.3 g (0.25 mol) of 5-bromonicotinic acid chloride in 170 ml of absolute tetrahydrofuran are slowly added dropwise and refluxed for a further hour. The reaction mixture is cooled in an ice bath and carefully mixed with 508 ml of 2N sulphuric acid. The organic phase is separated off, dried over sodium sulphate and concentrated by evaporation. The residue is taken up in 83 ml of water, 127 ml of glacial acetic acid and 16.6 ml of concentrated sulphuric acid and refluxed for 18 hours. The reaction solution is evaporated down, the residue is diluted with 200 ml of water and adjusted to pH 8 with sodium hydroxide solution. It is then extracted with chloroform, dried over sodium sulphate and evaporated down.

Yield: 15.2 g (30.4% of theory).
Melting point: 78°–80° C.

| | | | | |
|---|---|---|---|---|
| Calculated: | C 42.03 | H 3.01 | N 7.00 | Br 39.95 |
| Found: | 42.20 | 3.30 | 6.82 | 40.06 |

EXAMPLE B

5-Bromo-3-bromoacetyl-pyridine hydrobromide 4 g (0.02 mol) of 5-bromo-3-acetyl-pyridine are dissolved in 50 ml of chloroform, 5 drops of glacial acetic acid/hydrobromic acid (35%) are added and the mixture is heated to boiling. To this boiling solution, 3.2 g (0.02 mol) of bromine in 30 ml of chloroform are added dropwise over a period of 5 hours with stirring. After cooling to ambient temperature the yellow solid product is suction filtered.

Yield: 5 g (70% of theory).
Melting point: 225° C. (decomp.).

| | | | | |
|---|---|---|---|---|
| Calculated: | C 23.35 | H 1.67 | N 3.88 | Br 66.60 |
| Found: | 23.30 | 1.73 | 3.81 | 66.40 |

EXAMPLE C

2-(6-Chloro-pyridin-2-yl)-morpholin-5-one 6 g (0.0347 mol) of 2-hydroxy-2-(2-chloro-pyridin-6-yl)-ethanamine are dissolved in 160 ml of absolute toluene and mixed with 2.2 g (0.047 mol) of 50% sodium hydride in oil and stirred for 40 minutes at ambient temperature. Then 4.16 g (0.034 mol) of ethyl chloroacetate are added dropwise. The reaction mixture is stirred for 18 hours at ambient temperature and then carefully mixed with 10 ml of ethanol and 30 ml of water and subsequently acidified with dilute hydrochloric acid. The reaction solution is made alkaline with ammonia and extracted with methylene chloride. The organic phase is dried over sodium sulphate, concentrated by evaporation and the residue is purified over a silica gel column using ethyl acetate as eluant.

Yield: 1 g (14% of theory).

| | | | |
|---|---|---|---|
| Calculated: | C 50.83 | H 4.26 | N 13.17 |
| Found: | 50.55 | 4.11 | 13.30 |

EXAMPLE D

2-(6-Chloro-pyridin-2-yl)-morpholine 1 g (0.0047 mol) of 2-(6-chloro-pyridin-2-yl)-morpholin-5-one are dissolved in 20 ml of absolute tetrahydrofuran, added with stirring at ambient temperature to 5 ml of a 1 molar solution of borane in tetrahydrofuran and the reaction solution is stirred for 60 minutes. Then sufficient borane/tetrahydrofuran solution is added in batches until all the starting material has reacted, according to thin layer chromatography. The solvent is then drawn off, the residue is stirred in 20 ml of methanol for 18 hours and then evaporated down. This residue is taken up in 20 ml of 2N hydrochloric acid and stirred at 50° C. for 2 hours. The acid solution is cooled in an ice bath, made alkaline with ammonia solution and extracted with methylene chloride. The organic phase is dried over sodium sulphate, concentrated by evaporation and the residue is purified over a silica gel column with methanol as eluant.

Yield: 0.4 g (43% of theory).

| | | | | |
|---|---|---|---|---|
| Calculated: | C 54.42 | H 5.57 | N 14.10 | Cl 17.84 |
| Found: | 54.30 | 5.70 | 13.90 | 18.01 |

EXAMPLE E

N-[2-(4-(2-Hydroxyethoxy)-phenyl)-1-methylethyl]-2-hydroxy-2-(6-chloro-pyridin-2-yl)-ethanamine 21.2 g (0.122 mol) of 2-hydroxy-2-(6-chloro-pyridin-2-yl)-ethanamine and 21 g (0.108 mol) of 1-(4-(2-hydroxyethoxy)-phenyl)-propan-2-one are dissolved in 500 ml of absolute methanol, mixed with 7.3 g (0.122 mol) of acetic acid and 7.2 g (0.114 mol) of sodium cyanoborohydride and stirred overnight at ambient temperature. Then 300 ml of methanol are distilled off in vacuo, diluted with 400 ml of water, acidified with hydrochloric acid and then extracted three times with 250 ml of methylene chloride. The aqueous phase is then made alkaline with ammonia and extracted with methylene chloride. The organic phase obtained is dried over sodium sulphate and concentrated by evaporation, and the oil obtained initially crystallises out after a short time.

Yield: 23 g (60.7% of theory).
Melting point: 100°–102° C.

| Calculated: | C 61.62 | H 6.60 | N 7.98 | Cl 10.10 |
|---|---|---|---|---|
| Found: | 61.48 | 6.64 | 7.86 | 10.28 |

EXAMPLE F

N-[2-(4-(2-Hydroxyethoxy)-phenyl)-1-methylethyl]-2-(6-chloro-pyridin-2-yl)-morpholin-5-one 1 g (0.0285 mol) of N-[2-(4-(2-hydroxyethoxy)-phenyl)-1-methyl-ethyl]-2-hydroxy-2-(6-chloro-pyridin-2-yl)-ethanamine is dissolved in 40 ml of methylene chloride, 0.28 g (0.00285 mol) of triethylamine are added and then 0.322 g (0.00285 mol) of chloroacetyl chloride are added dropwise thereto with stirring in an ice bath. The reaction solution is stirred at ambient temperature for 40 minutes and evaporated down. The residue is dissolved in 10 ml of dimethylformamide, 110 mg (0.00234 mol) of 50–55% sodium hydride in oil are added and the resulting mixture is stirred for 30 minutes at ambient temperature. It is then carefully decomposed with 30 ml of water, acidified with 2N hydrochloric acid and then made alkaline with 2N ammonia. The product is extracted with methylene chloride, dried over sodium sulphate and concentrated by evaporation. The residue is purified over a silica gel column using ethyl acetate as eluant.

Yield: 0.7 g (76.5% of theory).

| Calculated: | C 61.45 | H 5.93 | N 7.16 | Cl 9.06 |
|---|---|---|---|---|
| Found: | 61.30 | 5.88 | 7.30 | 8.88 |

EXAMPLE 1

N-[2-(4-Carbomethoxymethoxyphenyl)-1-methylethyl]-2-hydroxy-2-(5-bromo-pyridin-3-yl)-morpholine 3.8 g (0.0142 mol) of N-(2-hydroxyethyl)-2-(4-carbomethoxyphenyl)-1-methyl-ethylamine are stirred with 5 g (0.0142 mol) of 5-bromo-3-bromoacetylpyridine hydrobromide and 5.6 g (0.056 mol) of potassium hydrogen carbonate in 300 ml of acetone for 2 hours at ambient temperature. Then 1.4 g (0.014 mol) of triethylamine are added and the mixture is stirred for a further 60 minutes at 30° to 40° C. After the mixture has been suction filtered and the filtrate concentrated, the oily residue is purified over a silica gel column using toluene/ethyl acetate (60/40) as eluant.

Yield: 1.4 g oil (21% of theory).

| Calculated: | C 54.20 | H 5.42 | N 6.02 |
|---|---|---|---|
| Found: | 54.07 | 5.31 | 6.19 |

According to ¹H-NMR spectrum (400 MHz, CDCl₃/CD₃OD) there is an approximately 1:1 mixture of the pairs of diastereoisomers.
delta=1.07 ppm (d, 3H).
delta=0.98 ppm (d, 3H).

EXAMPLE 2

N-[2-(4-Carboethoxymethoxyphenyl)-1-methylethyl]-2-hydroxy-2-(5-bromo-pyridin-3-yl)-morpholine Prepared analogously to Example 1 by reacting 1.0 g (0.007 mol) of N-(2-hydroxyethyl)-2-(4-carboethoxyphenyl)-1-methyl-ethylamine with 2.5 g (0.007 mol) of 5-bromo-3-bromoacetyl-pyridine hydrobromide, 2.8 g (0.028 mol) of potassium hydrogen carbonate and 0.7 g (0.007 mol) of triethylamine in 150 ml of acetone.

Yield: 1 g of oil (30% of theory),

| Calculated: | C 55.12 | H 5.68 | N 5.85 |
|---|---|---|---|
| Found: | 54.98 | 5.57 | 5.83 |

According to ¹H-NMR spectrum (400 MHz, CDCl₃/CD₃OD) there is an approximately 1:1 mixture of the pairs of diastereoisomers.
delta=1.07 ppm (d, 3H),
delta=0.98 ppm (d, 3H).

EXAMPLE 3

N-[2-(4-Carbomethoxymethoxyphenyl)-1-methylethyl]-2-(6-chloro-pyridin-2-yl)-morpholine 0.35 g (0.00176 mol) of 2-(6-chloro-pyridin-2-yl)-morpholine and 0.39 g (0.00176 mol) of 1-(4-carbomethoxymethoxyphenyl)-propan-2-one are dissolved in 20 ml of methanol, 0.1 g (0.00176 mol) of acetic acid and 0.11 g (0.00176 mol) of sodium cyanoborohydride are added and the mixture is stirred for 20 minutes at ambient temperature. It is then mixed with ice water, acidified with hydrochloric acid, made alkaline with ammonia solution, the product is extracted with methylene chloride, dried with sodium sulphate and evaporated down in vacuo. The residue is purified over a silica gel column using toluene/ethyl acetate (50:50) as eluant.

Yield: 0.6 g oil (84% of theory),

| Calculated: | C 62.29 | H 6.22 | N 6.92 |
|---|---|---|---|
| Found: | 62.35 | 6.17 | 6.74 |

According to ¹H-NMR spectrum (400 MHz, CDCl₃/CD₃OD) there is an approximately 1:1 mixture of the pairs of diastereoisomers.
delta=0.988 ppm (d, 3H),
delta=0.958 ppm (d, 3H).

EXAMPLE 4

N-[2-(4-Carboxymethoxyphenyl)-1-methylethyl]-2-(6-chloro-pyridin-2-yl)-morpholine 0.2 g (0.000453 mol) of N-[2-(4-carbomethoxymethoxyphenyl)-1-methylethyl]-2-(6-chloro-pyridin-2-yl)morpholine are dissolved in 1 ml of methanol, mixed with 1 ml of dioxan and 2 ml of 1N sodium hydroxide solution and stirred for 30 minutes at ambient temperature. Then the mixture is neutralised with 1.8 ml of 1N hydrochloric acid, extracted with chloroform, dried over sodium sulphate and evaporated down. The residue is triturated with ether and suction filtered.

Yield: 0.12 g (68% of theory).

Melting point: from 60° C. (decomp.).

| Calculated: | C 61.45 | H 5.93 | N 7.17 |
|---|---|---|---|
| Found: | 61.28 | 5.79 | 7.08 |

According to $^1$H-NMr spectrum (400 MHz, CDCl$_3$/CD$_3$OD) there is an approximately 1:1 mixture of the pairs of diastereoisomers.

delta=1.11 ppm (d, 3H),
delta=1.12 ppm (d, 3H).

EXAMPLE 5

N-[2-(4-(2-Hydroxyethoxy)-phenyl)-1-methylethyl]-2-(6-chloro-pyridin-2-yl)-morpholine 0.7 g of N-[2-(4-(2-hydroxyethoxy)-phenyl)-1-methylethyl]-2-(6-chloro-pyridin-2-yl)-morpholin-5-one are dissolved in 20 ml of tetrahydrofuran and over a period of 3 hours at ambient temperature 3 times 4 ml of a 1 molar borane/tetrahydrofuran solution are added. Then 30 ml of acetone are added and the mixture is evaporated down. The residue is dissolved in 100 ml of methanol and stirred for 20 hours. The solvent is distilled off in vacuo and the residue is purified over a silica gel column with ethyl acetate as eluant.

Yield: 0.6 g of oil (89% of theory),

| Calculated: | C 63.73 | H 6.69 | N 7.43 |
|---|---|---|---|
| Found: | 63.84 | 6.58 | 7.32 |

According to $^1$H-NMR spectrum (400 MHz, CDCl$_3$) there is an approximately 1:1 mixture of the pairs of diastereoisomers.

delta=0.962 ppm (d, 3H),
delta=0.930 ppm (d, 3H),

EXAMPLE 6

N-[2-(4-(2-Hydroxyethoxy)-phenyl-1-methylethyl]-2-(6-chloro-pyridin-2-yl)-morpholine 0.1 g (0.000246 mol) of N-[2-(4-carbomethoxymethoxyphenyl)-1-methylethyl]-2-(6-chloro-pyridin-2-yl)morpholine are dissolved in 10 ml of absolute tetrahydrofuran and over the course of 1 hour 5.5 mg (0.0005 mol) of lithium borohydride are added twice. The reaction solution is stirred for 20 hours at ambient temperature, evaporated down and the residue is carefully mixed with 15 ml of methanol and 0.5 ml of concentrated hydrochloric acid. The mixture is then made alkaline with ammonia solution, extracted with methylene chloride, dried over sodium sulphate and evaporated down in vacuo. The residue is purified over a silica gel column using toluene/ethyl acetate 50:50 as eluant.

Yield: 0.075 g oil (81% of theory),

| Calculated: | C 63.73 | H 6.69 | N 7.43 |
|---|---|---|---|
| Found: | 63.69 | 6.55 | 7.40 |

According to $^1$H-NMR spectrum (400 MHz, CDCl$_3$/CD$_3$OD) there is an approximately 1.3:1 mixture of the pairs of diastereoisomers.

delta=0.990 ppm (d, 3H),
delta=0.965 ppm (d, 3H),

EXAMPLE 7

N-[2-(4-Carbomethoxymethoxyphenyl)-1-methylethyl]-2-(pyridin-3-yl)-morpholine 1.80 g (6.73 mmol) of N-(2-hydroxyethyl)-2-(4-carbomethoxymethoxyphenyl)-1-methyl-ethylamine are stirred with 1.74 g (6.2 mmol) of 3-bromoacetyl-pyridinehydrobromide and 2.44 g (24.5 mmol) of potassium hydrogen carbonate in 50 ml of acetone for 24 hours at ambient temperature. The inorganic salts are filtered off and the filtrate is evaporated down using a rotary evaporator. The residue obtained is dissolved in 20 ml of trifluoroacetic acid and reduced with 1.39 ml ($8.68 \times 10^{-3}$ mol) of triethylsilane whilst cooling with ice. After 1 hour of ice cooling and 12 hours at ambient temperature the solution obtained is evaporated down. The residue is mixed with ice and made alkaline with concentrated ammonia. The aqueous solution is extracted three times with methylene chloride, the organic phases are combined, dried, filtered and concentrated using a rotary evaporator. The oil obtained is purified over a silica gel column using ethyl acetate as eluant. The hydrochloride is precipitated from isopropanol and ether with ethereal hydrochloric acid.

Yield: 0.5 (18% of theory),
Melting point: 190°–192° C. (decomp.),

| Calculated: | C 56.89 | H 6.37 | N 6.32 |
|---|---|---|---|
| Found: | 56.79 | 6.22 | 6.23 |

According to $^1$H-NMR spectrum (400 MHz, CDCl$_3$/CD$_3$OD) there is an approximately 1:1 mixture of the pairs of diastereoisomers.

EXAMPLE 8

N-[2-(4-Carbomethoxymethoxyphenyl)-1-methylethyl]-2-hydroxy-2-(pyrazin-2-yl)-morpholine Prepared analogously to Example 1 by reacting N-(2-hydroxyethyl)-2-(4-carbomethoxymethoxyphenyl)-1-methyl-ethylamine with 2-bromoacetyl-pyrazinehydrobromide in the presence of potassium hydrogen carbonate. The product is purified over silica gel using ethyl acetate/cyclohexane (9:1) as eluant.

Yield: 46% of theory, oil.

| Calculated: | C 62.00 | H 6.50 | N 10.85 |
|---|---|---|---|
| Found: | 61.90 | 6.61 | 10.76 |

According to $^1$H-NMR spectrum (400 MHz, CDCl$_3$/CD$_3$OD) there is an approximately 1:1 mixture of the pairs of diastereoisomers.

delta =1.01 ppm (d, 3H).
delta =1.03 ppm (d, 3H).

EXAMPLE 9

N-[2-(4-Carbomethoxymethoxyphenyl)-1-methylethyl]-2-hydroxy-2-(pyridin-2-yl)-morpholine Prepared analogously to Example 1 by reacting N-(2-hydroxymethyl)-2-(4-carbomethoxymethoxyphenyl)-1-methyl-ethylamine with 2-bromoacetyl-pyridinehydrobromide in the presence of potassium hydrogen carbonate. The product is purified over silica gel using toluene/ethyl acetate (1:1) as eluant.

Yield: 11% of theory, oil.

| Calculated: | C 65.27 | H 6.78 | N 7.25 |
|---|---|---|---|
| Found: | 65.34 | 6.89 | 7.13 |

According to ¹H-NMR spectrum (400 MHz, CDCl₃/CD₃OD) there is an approximately 1:1 mixture of the pairs of diastereoisomers.
delta=1.00 ppm (d, 3H).
delta=1.02 ppm (d, 3H).

EXAMPLE 10

N-[2-(4-Carbomethoxymethoxyphenyl)-1-methylethyl]-2-hydroxy-2-(pyridin-4-yl)-morpholine Prepared analogously to Example 1 by reacting N-(2-hydroxyethyl)-2-(4-carbomethoxymethoxyphenyl)-1-methyl-ethylamine with 4-bromoacetyl-pyridine-hydrobromide in the presence of potassium hydrogen carbonate. The product is purified over silica gel using ethyl acetate as eluant.
Yield: 43% of theory, oil.

| Calculated: | C 65.27 | H 6.78 | N 7.25 |
|---|---|---|---|
| Found: | 65.30 | 6.73 | 7.22 |

According to ¹H-NMR spectrum (400 MHz, CDCl₃/CD₃OD) there is an approximately 1:1 mixture of the pairs of diastereoisomers.
delta=0.979 ppm (d, 3H).
delta=1.000 ppm (d, 3H).

EXAMPLE 11

N-[2-(4-(2-Hydroxyethoxy)-phenyl)-1-methylethyl]-2-(6chloro-pyridin-2-yl)-morpholine-N-oxide 0.13 g (0.34 mmol) of a 1:1 mixture of N-[2-(4-(2-hydroxyethoxy)-phenyl)-1-methylethyl]-2-(6-chloro-pyridin-2-yl)-morpholine are dissolved in 2 ml of acetic acid and heated with 40 mg of hydrogen superoxide for 1.5 hours to 85° C. and then evaporated to dryness. The residue is mixed with ice, made alkaline with ammonia and extracted with methylene chloride. The organic phase is dried and evaporated to dryness at 20° C. The residue is purified over a silica gel column using methylene chloride/methanol (8:2) as eluant.
Yield: 60 mg (45% of theory).
Melting point: 94° C. (decomp.).

| Calculated: | C 61.14 | H 6.41 | N 7.13 |
|---|---|---|---|
| Found: | 61.22 | 6.50 | 7.08 |

According to ¹H-NMR spectrum (400 MHz, DMSO/CD₃OD) the compound is present as pure diastereoisomer A.
delta=1.18 ppm (d, 3H).

EXAMPLE 12

N-[2-(4-(2-Hydroxyethoxy)-phenyl)-1-methylethyl]-2-(6-chloro-pyridin-2-yl)-morpholine Pair of diastereoisomers A
3 g of a 1:1 mixture of the pairs of diastereoisomers of N-[2-(4-(2-hydroxyethoxy)-phenyl)-1-methylethyl]-2-(6-chloro-pyridin-2-yl)-morpholine are dissolved in ether and the hydrochloride is precipitated with diisopropylether/hydrochloric acid. The salt is dissolved in 50 ml of acetone and evaporated to dryness. The residue is decocted with 30 ml of acetone and cooled to ambient temperature, whilst crystallisation occurs after trituration.
Yield: 1.3 g (43% of theory).
Melting point of the hydrochloride: 196°–198° C..

| Calculated: | C 58.11 | H 6.34 | N 6.78 | Cl 17.16 |
|---|---|---|---|---|
| Found: | 57.93 | 6.47 | 6.78 | 17.03 |

¹H-NMR spectrum of the base (400 MHz, CDCl₃):
delta=4.610 ppm (dd, >C̲H̲ OH)
Pair of diastereoisomers B
The mother liquor is evaporated to dryness and the residue obtained is dried in vacuo.
Yield: 1.7 g (56% of theory).
Melting point of the hydrochloride: from 70° C. (decomp.).

| Calculated: | C 58.11 | H 6.34 | N 6.78 | Cl 17.16 |
|---|---|---|---|---|
| Found: | 58.00 | 6.21 | 6.70 | 17.20 |

¹H-NMR spectrum of the base (400 MHz, CDCl₃):
delta=4.640 ppm (dd, >C̲H̲—OH).

EXAMPLE I

Coated tablet containing 10 mg of
N-[2-(4-(2-hydroxyethoxy)-phenyl)-1-methyl-ethyl]-2-(6-chloro-pyridin-2-yl)-morpholine Composition
1 coated tablet contains:

| (1) Active substance | 10.0 mg |
|---|---|
| (2) Lactose | 69.0 mg |
| (3) Corn starch | 35.0 mg |
| (4) Polyvinylpyrrolidone | 5.0 mg |
| (5) Magnesium stearate | 1.0 mg |
| | 120.0 mg |

Method
(1)+(2)+(3) are mixed together and moistened with (4) in an aqueous solution. The moist mass is passed through a screen with a mesh size of 1.6 mm and dried at 45° C. in a circulating air dryer. The dry granules are passed through a screen with a mesh size of 1 mm and mixed with (5). The finished mixture is compressed to form tablet cores.
Weight of core: 120.0 mg.
Diameter: 7.0 mm.
Radius of curvature: 6.0 mm.
The tablet cores thus produced are coated in known manner with a coating consisting essentially of sugar and talc. This coating may also contain colouring extracts. The finished coated tablets are polished with beeswax.
Weight of coated tablet: 180.0 mg.

EXAMPLE II

Coated tablet containing 50 mg of
N-[2-(4-(2-hydroxyethoxy)-phenyl)-1-methyl-ethyl]-2-(6-chloro-pyridin-2-yl)-morpholine Composition
1 coated tablet contains:

| (1) Active substance | 50.0 mg |
|---|---|
| (2) Lactose | 110.8 mg |

-continued

|   |   |
|---|---|
| (3) Corn starch | 50.0 mg |
| (4) Polyvinylpyrrolidone | 8.0 mg |
| (5) Magnesium stearate | 1.2 mg |
|   | 220.0 mg |

Method
The method is the same as in Example I.
Weight of core: 220.0 mg.
Diameter: 9.0 mm.
Radius of curvature: 8.0 mm.
Weight of coated tablet: 300.0 mg.

EXAMPLE III

Tablets containing 150 mg of
N-[2-(4-(2-hydroxyethoxy)-phenyl)-1-methylethyl]-2-(6-chloro-pyridin-2-yl)-morpholine Composition
1 tablet contains:

|   |   |
|---|---|
| (1) Active substance | 150.0 mg |
| (2) Lactose | 86.0 mg |
| (3) Corn starch | 50.8 mg |
| (4) Microcrystalline cellulose | 25.0 mg |
| (5) Polyvinylpyrrolidone | 7.0 mg |
| (6) Magnesium stearate | 1.2 mg |
|   | 320.0 mg |

Method
(1)+(2)+(3)+(4)+(5) are mixed together and moistened with water. The moist mass is passed through a screen with a mesh size of 1.6 mm and dried at 45° C. The dry granules are passed through the same screen again and mixed with (6). Tablets are compressed from the finished mixture.
Weight of tablet: 320.20 mg.
Diameter: 10.0 mm.
The tablets are provided with a dividing notch in order to make it easier to break the tablets in half.

EXAMPLE IV

Hard gelatin capsules containing 100 mg of
N-[2-(4-(2-hydroxyethoxy)-phenyl)-1-methylethyl]-2-(6-chloro-pyridin-2-yl)-morpholine Composition
1 capsule contains:
Capsule casing: hard gelatin capsules size 3
Capsule contents:

|   |   |
|---|---|
| (1) Active substance | 100.0 mg |
| (2) Lactose × 1H$_2$O | 38.0 mg |
| (3) Corn starch, dried | 60.0 mg |
| (4) Magnesium stearate | 2.0 mg |
| Weight of capsule filling: | 200.0 mg |
| (5) Distilled water | q.s. |

Method
A small amount of lactose is dissolved in distilled water (granulating liquid) to form an approximately 10% solution. The active substance, the remaining lactose and corn starch are mixed together and moistened with the granulating liquid. The mass is screened, dried and, after being screened once more, homogeneously mixed with magnesium stearate. The fine granules are packed into capsules in a suitable machine.

EXAMPLE V

Hard gelatin capsules containing 200 mg of
N-[2-(4-(2-hydroxyethoxy)-phenyl)-1-methylethyl]-2-(6-chloro-pyridin-2-yl)-morpholine COMPOSITION
Capsule casing: hard gelatin capsules size 1
Capsule contents:

|   |   |
|---|---|
| (1) Active substance | 200.0 mg |
| (2) Lactose × 1H$_2$O | 47.0 mg |
| (3) Corn starch, dried | 70.0 mg |
| (4) Magnesium stearate | 3.0 mg |
| Weight of capsule filling: | 320.0 mg |
| (5) Distilled water | q.s. |

Method
A small amount of lactose is dissolved in distilled water (granulating liquid) to form an approximately 10% solution. The active substance, the remaining lactose and corn starch are mixed together and moistened with the granulating liquid. The mass is screened, dried and, after being screened once more, homogeneously mixed with magnesium stearate. The fine granules are packed into capsules in a suitable machine.

EXAMPLE VI

COMPLETE FEED II FOR FATTENING PIGS

|   |   |
|---|---|
| Barley | 370 g/kg |
| Wheat flour | 200 g/kg |
| Manioc flour | 135 g/kg |
| Broad beans | 100 g/kg |
| Shredded rape extract | 100 g/kg |
| Edible fat | 65 g/kg |
| Lysine-rich mineral feed for pigs | 20 g/kg |
| Active substance premix | 10 g/kg |

These components in the quantities specified produce 1 kg of feed when carefully mixed together.
The 10 g of active substance premix contain for example 10 mg of active substance and 9.99 g of corn starch.

EXAMPLE VII

COMPLETE FEED II FOR BROILERS

|   |   |
|---|---|
| Maize | 625 g/kg |
| Soya bean flour | 260 g/kg |
| Meat meal | 40 g/kg |
| Edible fat | 25 g/kg |
| Soya oil | 17 g/kg |
| Bicalcium phosphate | 12 g/kg |
| Calcium carbonate | 6 g/kg |
| Vitamin/mineral mix | 5 g/kg |
| Active substance premix | 10 g/kg |

These components in the quantities specified produce 1 kg of feed when carefully mixed together.
The 10 g of active substance premix contain for example 10 mg of active substance and 9.99 g of corn starch.

EXAMPLE VIII

CONCENTRATED FEED FOR CATTLE

|   |   |
|---|---|
| Shredded sugar beet | 600.0 g/kg |
| Maize gluten | 100.0 g/kg |
| Malt germs | 50.0 g/kg |

-continued

| | |
|---|---|
| Soya bean flour | 35.0 g/kg |
| Wheat | 110.0 g/kg |
| Molasses | 60.0 g/kg |
| Edible phosphates | 12.0 g/kg |
| Calcium carbonate | 2.5 g/kg |
| Salt | 5.0 g/kg |
| Minerals | 10.0 g/kg |
| Vitamin premix | 5.5 g/kg |
| Active substance premix | 10.0 g/kg |

These components in the quantities specified produce 1 kg of feed when carefully mixed together.

The 10 g of active substance premix contain for example 10 mg of active substance and 9.99 g of corn starch.

EXAMPLE IX

FATTENING FEED FOR LAMBS

| | |
|---|---|
| Barley | 690 g/kg |
| Soya flour | 100 g/kg |
| Maize | 150 g/kg |
| Molasses | 30 g/kg |
| Vitamin/mineral mix | 20 g/kg |
| Active substance premix | 10 g/kg |

These components in the quantities specified produce 1 kg of feed when carefully mixed together.

The 10 g of active substance premix contain for example 10 mg of active substance and 9.99 g of corn starch.

What is claimed is:

1. A compound of formula

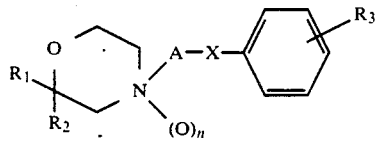

(I)

wherein

A is $C_2$–$C_3$ n-alkylene unsubstituted or mono-or di-substituted by methyl or ethyl, X is $(O)_m$, wherein m is 1 or 0

$R_1$ is a heteroaromatic 6-membered ring containing 1 or 2 nitrogen atoms and unsubstituted or substituted by halo, hydrogen, trifluoromethyl or alkyl, $R_2$ is hydrogen or hydroxy, $R_3$ is hydroxy, alkoxy, carboxy, alkoxycarbonyl, aminocarbonyl, alkylaminocarbonyl or dialkylaminocarbonyl, $C_1$–$C_6$ alkoxy substituted in the end position by carboxy, alkoxycarbonyl, aminocarbonyl, alkylaminocarbonyl or dialkylaminocarbonyl, $C_2$–$C_7$ alkoxy substituted in the end position by hydroxy, alkoxy or phenylalkoxy, or ethenylene unsubstituted or substituted by alkyl and substituted in the end position by carboxy, alkoxycarbonyl, aminocarbonyl, alkylaminocarbonyl, dialkylaminocarbonyl, pyrrolidino, piperidino or hexamethyleneimino and n is 0 or 1, where all the alkyl or alkoxy groups mentioned hereinbefore without carbon limitation may contain from 1 to 3 carbon atoms, the optical isomer, diastereoisomer or acid addition salt thereof.

2. The compound as recited in claim 1, wherein

A is ethylene or n-propylene unsubstituted or substituted by methyl,

X is $(O)_m$ wherein m is O, $R_1$ is pyridinyl unsubstituted or substituted by chlorine or bromine, or pyrazinyl, pyrimidinyl or pyridazinyl, $R_2$ is hydrogen or hydroxy, and $R_3$ is carboxy, methoxycarbonyl, ethoxycarbonyl, aminocarbonyl, carboxymethoxy, methoxycarbonylmethoxy, ethoxycarbonylmethoxy, aminocarbonylmethoxy, methylaminocarbonylmethoxy, 2-hydroxy-ethoxy, 2-ethoxt-ethoxy, 2-phenethoxy-ethoxy, 6-hydroxy-n-hexoxy or 2-carbomethoxy-1-methyl-ethenyl group, the optical isomer, diastereoisomer or acid addition salt thereof.

3. A compound of formula

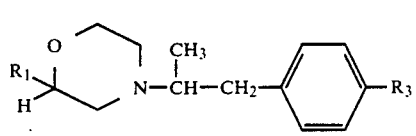

(Ia)

wherein $R_1$ is pyridin-2-yl substituted in the 6-position by chlorine or bromine or by methyl or trifluoromethyl and $R_3$ is carboxymethoxy, carbomethoxymethoxy, ethoxycarbonylmethoxy, aminocarbonylmethoxy, methylaminocarbonylmethoxy, 2-hydroxy-ethoxy, 2-ethoxy-ethoxy or 2-carbomethoxy-1-methylethenyl, the optical isomer, diastereoisomer or acid addition salt thereof.

4. The compound as recited in claim 1, N-[2-(4-carbomethoxymethoxyphenyl)-1-methylethyl]-2-(6-chloro-pyridin-2-yl)-morpholine, the optical isomer, diastereoisomer or acid addition salt thereof.

5. The compound as recited in claim 1, N-[2-(4-carboxymethoxyphenyl)-1-methylethyl]-2-(6-chloro-pyridin-2-yl)-morpholine, the optical isomer, diastereoisomer or acid addition salt thereof.

6. The compound as recited in claim 1, N-[2-(4-(2-hydroxyethoxy)-phenyl)-1-methylethyl]-2-(6-chloropyridin-2-yl)-morpholine, the optical isomer, diastereoisomer or acid addition salt thereof.

7. The compound as recited in claim 1 wherein the acid addition salt is physiologically acceptable.

8. The compound as recited in claim 3 wherein the acid addition salt is physiologically acceptable.

9. A pharmaceutical composition useful in the treatment of diabetes mellitus in a warm-blooded animal comprising a pharmaceutically effective amount of a compound as recited in claim 1 together with an inert carrier or diluent.

10. A pharmaceutical composition useful in the treatment of diabetes mellitus in a warm-blooded animal comprising a pharmaceutically effective amount of a compound as recited in claim 3 together with an inert carrier or diluent.

11. A method for treating diabetes mellitus in a warm-blooded animal which comprises administering to said animal a therapeutically effective amount of a compound as recited in claim 1.

12. A method for treating obesity in a warm-blooded animal which comprises administering to said animal a therapeutically effective amount of a compound as recited in claim 1.

13. A method for preventing or treating atherosclerotic changes in a warm-blooded animal which comprises administering to said animal a therapeutically effective amount of compound as recited in claim 1.

14. A method for enhancing animal performance to promote and accelerate growth, milk and hair production and to improve the utilization of feed, the quality of carcasses and to shift the ratio of meat to fat in favor of meat which comprises administering to an animal a performance-enhancing amount of a compound as recited in claim 1.

15. A method for treating diabetes mellitus in a warm-blooded animal which comprises administering to said animal a therapeutically effective amount of a compound as recited in claim 3.

16. A method for treating obesity in a warm-blooded animal which comprises administering to said animal a therapeutically effective amount of a compound as recited in claim 3.

17. A method for preventing or treating atherosclerotic changes in a warm-blooded animal which comprises administering to said animal a therapeutically effective amount of a compound as recited in claim 3.

18. A method for enhancing animal performance to promote and accelerate growth, milk and hair production and to improve the utilization of feed, the quality of carcasses and to shift the ratio of meat to fat in favor of meat which comprises administering to an animal a performance-enhancing amount of a compound as recited in claim 3.

19. A pharmaceutical composition useful in the treatment of obesity in a warm-blooded animal comprising a pharmaceutically effective amount of a compound as recited in claim 1 together with an inert carrier or diluent.

20. A pharmaceutical composition useful in the treatment of obesity in a warm-blooded animal comprising a pharmaceutically effective amount of a compound as recited in claim 3 together with an inert carrier or diluent.

21. A pharmaceutical composition useful in preventing and treating atherosclerotic changes in a warm-blooded animal comprising a pharmaceutically effective amount of a compound as recited in claim 1 together with an inert carrier or diluent.

22. A pharmaceutical composition useful in preventing and treating atherosclerotic changes in a warm-blooded animal comprising a pharmaceutically effective amount of a compound as recited in claim 3 together with an inert carrier or diluent.

* * * * *